(12) United States Patent
Tsukamoto et al.

(10) Patent No.: US 11,254,917 B2
(45) Date of Patent: Feb. 22, 2022

(54) METHOD OF PROMOTING SPHEROID FORMATION

(71) Applicants: TOPPAN PRINTING CO., LTD., Tokyo (JP); OSAKA UNIVERSITY, Suita (JP)

(72) Inventors: Kei Tsukamoto, Tokyo (JP); Shinji Irie, Tokyo (JP); Michiya Matsusaki, Osaka (JP)

(73) Assignees: TOPPAN PRINTING CO., LTD., Tokyo (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 16/104,533

(22) Filed: Aug. 17, 2018

(65) Prior Publication Data
US 2018/0355322 A1    Dec. 13, 2018

Related U.S. Application Data

(63) Continuation of application No. PCT/JP2017/006687, filed on Feb. 22, 2017.

(30) Foreign Application Priority Data

Feb. 22, 2016  (JP) .............................. JP2016-031159

(51) Int. Cl.
| | |
|---|---|
| *C12N 5/07* | (2010.01) |
| *C12N 5/071* | (2010.01) |
| *C12N 5/09* | (2010.01) |
| *C12M 3/00* | (2006.01) |

(52) U.S. Cl.
CPC ............ *C12N 5/0693* (2013.01); *C12M 3/00* (2013.01); *C12N 5/06* (2013.01); *C12N 5/0697* (2013.01); *C12N 2500/34* (2013.01); *C12N 2501/90* (2013.01); *C12N 2501/91* (2013.01); *C12N 2502/1323* (2013.01); *C12N 2502/28* (2013.01); *C12N 2513/00* (2013.01); *C12N 2527/00* (2013.01)

(58) Field of Classification Search
CPC .... C12N 5/06; C12N 5/0697; C12N 2501/90; C12N 2527/00; C12N 2513/00; C12N 2501/91

See application file for complete search history.

(56) References Cited

U.S. PATENT DOCUMENTS

2018/0305669 A1*  10/2018  Hancock .............. C12N 5/0671

FOREIGN PATENT DOCUMENTS

| JP | 4159103 | 10/2008 |
|---|---|---|
| JP | 2011-41472 | 3/2011 |
| JP | 5322332 | 10/2013 |
| JP | 5322333 | 10/2013 |
| JP | 5578648 | 8/2014 |
| JP | 2014204674 A | * 10/2014 |
| JP | 5822217 | 11/2015 |
| WO | WO 2011/077894 A1 | 6/2011 |

OTHER PUBLICATIONS

Hou et al. Effect of a hepatocyte growth factor/heparin-immobilized collagen system on albumin synthesis and spheroid formation by hepatocytes. Journal of Bioscience and Bioengineering vol. 110 No. 2, 208-216 (Year: 2010).*
Ivascu et al. Rapid Generation of Single-Tumor Spheroids for High-Throughput Cell Function and Toxicity Analysis. Journal of Biomolecular Screening 2006:922-932 (Year: 2006).*
MDA-MB-231. ATCC. downloaded from atcc.org/Products/All/HTB-26.aspx on Feb. 21, 2020. p. 1 (Year: 2020).*
Szatmari et al. The role of syndecan-1 in cellular signaling and its effects on heparan sulfate biosynthesis in mesenchymal tumors. Front.Oncol. 3:310. p. 1-11 (Year: 2013).*
Lei et al. Characterization of a multilayer heparin coating for biomolecule presentation to human mesenchymal stem cell spheroids. Biomater Sci. May 1, 2014; 2(5): 666-673. (Year: 2014).*
Heparin, Biotin conjugate. Sigma-Aldrich, downloaded from www.sigmaaldrich.com/catalog/product/mm/375054?lang=en&region=USlang=en&region=US. p. 1-3 (Year: 2020).*
Garzoni et al. Dissecting coronary angiogenesis: 3D co-culture of cardiomyocytes with endothelial or mesenchymal cells. Experimental Cell Research. 315 (2009): p. 3406-3418 (Year: 2009).*
Razian et al. Production of Large Numbers of Size-controlled Tumor Spheroids Using Microwell Plates. J. Vis. Exp. (81), e50665, doi: 10.3791/50665 (2013). p. 1-6 (Year: 2013).*
Nishiguchi et al. Cell—Cell Crosslinking by Bio-Molecular Recognition of Heparin-Based Layer-by-Layer Nanofilms. Macromol. Biosci. 2015, 15, 312-317 (Year: 2015).*
Davis, "Morphogensis by dissociated immature rat testicular cells in primary culture", Journal of Embryology & Experimental Morphology, vol. 44, pp. 297-302. Apr. 1978.
Folkman et al., "Self Regulation of growth in Three Dimensions", The Journal of Experimental Medicine, vol. 138(4), pp. 745-753, Oct. 1973.
Sutherland et al., "A multi-component radiation survival curve using in vitro tumour model" International Journal of Radiation Biology, vol. 18, No. 5, pp. 491-495, Oct. 1970.
International Search Report dated May 16, 2017 in corresponding International Patent Application No. PCT/JP2017/006687.

(Continued)

*Primary Examiner* — Taeyoon Kim (57) ABSTRACT

A method of promoting spheroid formation, including: a preparation step of preparing a mixture obtained by mixing a cell sample with a promoter; and a culture step of culturing, inside a spheroid formation-culture vessel, the mixture obtained in the preparation step, in which the promoter is a polymer in which one or more selected from the group consisting of D-glucosamine, D-galactosamine, D-glucuronic acid, L-iduronic acid, and D-galactose are polymerized.

5 Claims, 2 Drawing Sheets

(56) References Cited

OTHER PUBLICATIONS

Written Opinion of the International Searching Authority dated May 16, 2017 in corresponding International Patent Application No. PCT/JP2017/006687.
Ruei-Zhen Lin and Hwan-You Chang, "Recent Advances in Three-dimensional Multicellular Spheroid Culture for Biomedical Research", Biotechnol. J., 2008, vol. 3, No. 9-10, pp. 1172-1184 (13 pages).
Notice of Reasons for Rejection dated Jun. 16, 2020 in Japanese Patent Application No. 2016-031159.
John T. Wilson et al.; "Biomolecular Surface Engineering of Pancreatic Islets with Thrombomodulin"; National Institutes of Health; Acta Biomater, Jun. 2010; 6:1895-1903; (21 pages).

* cited by examiner

METHOD OF PROMOTING SPHEROID FORMATION

CROSS REFERENCE TO RELATED APPLICATIONS

This application is a continuation application based on a PCT Patent Application No. PCT/JP2017/006687, filed Feb. 22, 2017, whose priority is claimed on Japanese Patent Application No. 2016-031159, filed on Feb. 22, 2016, the entire contents of which are hereby incorporated by reference.

BACKGROUND OF THE INVENTION

Field of the Invention

The present invention relates to a method of promoting spheroid formation from a cell and a kit used for the method.

Description of the Related Art

In recent years, the cell and tissue engineering including iPS cell technology as a representative thereof has achieved remarkable development, and applications are being proceeded mainly in the medical field including regeneration medicine. For example, in the field of regenerative medicine, sheets formed from cells collected from patients have already been approved as artificial skin and artificial retina, and are supplied to clinical sites. In addition, methods for forming a ye-dimensional tissue structure like tissues in living body by stacking sheets formed from cells and constructing a vascular network in the sheets have also been reported (for example, refer to Japanese Patent No. 532332 and Japanese Patent No. 5322333).

As a method for forming a tissue maintaining a three-dimensional structure closer to a living body, a spheroid (cell aggregate) culture method using aggregation reaction inherent in adhesive cells is known conventionally (for example, Davis, Journal of Embryology & Experimental Morphology, 1978, vol. 44, p. 297-302; Folkman, et al., The Journal of Experimental Medicine, 1973, vo. 138(4), p. 745-753; and Sutherland, et al., International Journal of Radiation Biology, 1970, vol. 18(5), p. 491-495). In the spheroid culture method, a spheroid is formed by culturing adhesive cells on a non-adhesive scaffold or without using a scaffold. The formed spheroid is closer to a living tissue than a single-layered cell layer adhered onto the scaffold. For this reason, by using the spheroid, it is possible to more conveniently evaluate the effect of a drug on a living tissue.

In the spheroid culture method, several dedicated culture vessels for forming a spheroid have already been reported. As the dedicated culture vessel, for example, a culture vessel coated with functional molecules for realizing non-adhesive scaffold, a culture vessel with a cell non-adhesive gel attached on the surface thereof, a vessel for culture in microdroplets (culture vessel in microdroplet), and the like are commercially available. In addition, a culture vessel in which a plurality of cells with a minimum inner diameter of 3 μm or less are continuously formed and has an uneven structure functioning as a cell adhesion surface has also been reported (for example, refer to Japanese Patent No. 4159103). By culturing cells in such microcells, grown cells are not widely spread in a single layer but forms a spheroid.

SUMMARY

However, in the spheroid culture method, there is a case where formation is not possible depending on the kind of cells. In addition, variation easily occurs in uniformity of tissues of the formed spheroid and control is extremely difficult, in drug sensitivity test and the like using patient specimens in clinical sites and the like, the amount of the specimens that can be used is also limited. For this reason, instability in spheroid formation is always mentioned as a concern.

In addition, in the spheroid culture method, since adhesive force inherent in cells is used as driving force, it takes a long time to form a spheroid. Depending on the number of cells or the kind of cells, there is a case where it takes about three to seven days to form a spheroid, for example. There are only a small number of examples of a method for reducing the time required for spheroid formation that have been reported to the present.

In Japanese Patent No. 5822217 and Japanese Patent No. 5578648, methods for using body fluid of cephalopods such as cuttlefish, octopus, and eelpout, or fish are reported. However, these are derived from natural products, and thus are not suitable for reliable low cost preparation of a spheroid.

An object of the present invention is to provide a method for promoting spheroid formation capable of promoting cell aggregation and organization and forming a spheroid in a fast and stable manner, and to provide a kit for forming a spheroid by the method.

The method of promoting spheroid formation according to a first aspect of the present invention includes a preparation step of preparing a mixture obtained by mixing a cell sample with a promoter; and a culture step of culturing, inside a spheroid formation-culture vessel, the mixture obtained in the preparation step, wherein the promoter is a polymer in which one or more selected from the group consisting of D-glucosamine, D-galactosamine, D-glucuronic acid, D-glucuronic acid, and D-galactose are polymerized.

In the first aspect, the culture step may be performed, after repeatedly mixing the cell sample with the promoter in the preparation step.

In the first aspect, before the culture step, external force may be applied to cells in the mixture obtained by the preparation step.

In the first aspect, the external force may be centrifugal force.

In the first aspect, the number of cells included in the cell sample may be $1 \times 10^3$ to $1 \times 10^6$ cells.

In the first aspect, the cell sample may contain cells collected from animals.

In the first aspect, the cell sample may contain cells collected from humans.

In the first aspect, the promoter may be one selected from the group consisting of heparin, heparan sulfate, keratan sulfate, chondroitin sulfate, hyaluronic acid, and dermatan sulfate.

In the first aspect, the promoter may be one selected from the group consisting of heparin, chondroitin sulfate, and hyaluronic acid.

A kit for promoting spheroid formation in a second aspect of the present invention has a promoter including a polymer in which one or more selected from the group consisting of D-glucosamine, D-galactosamine, D-glucuronic acid, L-iduronic acid, and D-galactose are polymerized.

In the second aspect, the promoter may be one selected from the group consisting of heparin, heparan sulfate, keratan sulfate, hyaluronic acid, chondroitin sulfate, or dermatan sulfate.

The kit for promoting spheroid formation according to the second aspect may further include a spheroid formation-culture vessel.

By using a promoter having a specific polymer by using a method of promoting spheroid formation and a kit for promoting spheroid formation according to the aspects of the present invention, it is possible to form a spheroid in a fast and stable manner by convenient steps regardless of a culture vessel.

DETAILED DESCRIPTION OF THE PREFERRED EMBODIMENTS

A method for promoting spheroid formation according to a first embodiment of the present invention is a method for promoting spheroid formation including the following steps (1) and (2).

(1) A step of preparing a mixture obtained by mixing a cell sample with a promoter (preparation step).

(2) A step of culturing the mixture obtained in the step inside a spheroid formation-culture vessel (culture step).

In the method of promoting spheroid formation according to the embodiment, a promoter having a polymer having a specific structure is used. By mixing the promoter with cells, it is possible to form a spheroid in a faster and more reliable manner compared to performing formation using only adhesive force inherent in the cells as driving force. Although the reason why such an effect is obtained by the promoter is not clear, it is estimated that the promoter is adhered on a surface of a cell, and due to a layer formed by the promoter, aggregation or organization of cells becomes faster and more reliable.

In the method of promoting spheroid formation according to the embodiment, due to the effect of promoting spheroid formation by the promoter, it is possible to stably form a spheroid even in a case of using a cell having weak cohesive force between cells. That is, by the method of promoting spheroid formation according to the embodiment, it is possible to reliably form a spheroid even in a case of using a cell in which there is a difficulty in forming a spheroid. In addition, the spheroid formed by the method of promoting spheroid formation according to the embodiment has a shape close to a true sphere and is relatively uniform in size. Although the reason why a spheroid having a relatively uniform shape or size can be formed is not clear, it is estimated that, due to interaction between layers of promoter formed on the cell surface, adhesive force or cohesive force imparted between the cells in the system becomes almost constant.

The promotor used in the embodiment includes a polymer in which one or more selected from the group consisting of D-glucosamine, D-galactosamine, D-glucuronic acid, L-iduronic acid, and D-galactose are polomerized. D-glucosamine and the like constituent components of glycosaminoglycan (mucopolysaccharides d the polymer has a structure of glycosaminoglycan in at least a moiety. That is, the polymer has a lot of sulfate groups and carboxyl groups and is an electrolyte negatively charged. Glycosaminoglycan is a polymer known as a factor that significantly contributes to organization of cells or the like in a living body.

The promoter used in the embodiment may be glycosaminoglycan obtained by polymerization of one or more selected from the group consisting of D-glucosamine, D-galactosamine, D-glucuronic acid, L-iduronic acid, and D-galactose, or may be a poly which a molecule other than D-glucosamine and the like binds to the glycosaminoglycan. Examples of the molecule other than D-glucosamine and the like include saccharides other than D-glucosamine and the like, uronic acid, sugar chain, amino acid, peptide, fatty acid, lipid, and the like.

Examples of the promoter used in the embodiment include heparin, heparan sulfate, keratan sulfate, chondroitin sulfate, hyaluronic acid, or dermatan sulfate, and heparin, chondroitin sulfate, or hyaluronic acid is preferable. From a viewpoint of high effect of promoting spheroid formation and high versatility, heparin is more preferable.

In the embodiment, first, as the step (I), mix a cell sample in which a cell with which a spheroid is to be formed is suspended in a solvent with a promoter. By mixing the cell sample with the promoter, the promoter is adhered onto a surface of a cell in the cell sample. The promoter mixed with the cell sample may be one kind, or two or more kinds may be mixed and used.

The cell included in the cell sample used in the embodiment may be an adhesive cell, may be a cell collected from an animal, may be a cell obtained by culturing a cell collected from an animal, may be a cell obtained by performing various treatments on the cell collected from an animal, and may be a culture cell line. In a case where the cell included in the cell sample is a cell collected from an animal, the collection site is not particularly limited. The cell may be a body cell derived from bones, muscles, viscera, nerves, brain, skin, blood, and the like, and may be a reproductive cell, and may be an embryonic stem cell (ES cell). In addition, the kind of the animal from which the cell included in the cell sample is derived is not particularly limited. For example, cells derived from animals such as humans, monkeys, dogs, cats, rabbits, pigs, cows, mice, and rats may be used. The cell obtained by culturing a cell collected from an animal may be a primary culture cell, and may be a subculture cell. In addition, examples of the cell obtained by performing various treatments include an induced pluripotent stein cell (iPS cell) and a cell after induction of differentiation.

The cell sample used in the embodiment may include only one kind of cell, and may be a suspension including two or more kinds of cells. By using a cell sample including one kind of cell, it is possible to form spheroid including only one kind of cell. By using a cell sample including a plurality of kinds of cells, it is possible to form a spheroid including a plurality of kinds of cells.

The cell included in the cell sample used in the embodiment may be a cell in any cell cycle, may be an undifferentiated cell, and may be a cell after differentiation. In addition, the cell may be a normal cell, and may be a cell collected from a pathologic tissue such as a cancer tissue.

Examples of the cell included in the cell sample include, specifically, nerve cell, dendritic cell, immune cell, vascular endothelial cell, lymphatic endothelial cell, fibroblast, cancer cell such as hepatoma cell, epithelial cell, myocardial cell, liver cell, pancreatic islet cell, tissue stem cell, smooth muscle cell, d the like. For example, by using a cell sample including a cancer cell, it is possible to form a spheroid of the cancer cell in a faster and more stable manner. In addition, for example, by using a suspension including two or more kinds of cells such as cancer cell derived from humans, fibroblast, and vascular cell, it is possible to form a mixed spheroid imitating biological tissues.

The number of the cells included in the cell sample used in the embodiment is not particularly limited, and, considering the size of the objective spheroid to be formed, may be optionally set according to the culture environment. For example, by setting the number of the cells included in the cell sample to be $1\times10^3$ to $1\times10^6$ cells, it is possible to form a spheroid with a sufficient size for use in evaluation tests of pharmaceutical agents and the like. In a case where the number of the cells included in the cell sample is not sufficient for forming a spheroid with an objective size, before performing the step (1), culturing may be performed to proliferate cells until the number of the cells reaches the required number of cells.

The mixture of the cell sample and the promoter cultured in the step (2) is a cell suspension. For this reason, the cell sample is preferably a suspension obtained by suspending cells in a solvent. The cell sample may be a cell suspension in a state of being mixed with a promoter, and a cell suspension cultured in the step (2) may be prepared by mixing a pellet-like cell sample with a solution containing a promoter. The solvent for preparing the cell suspension is not particularly limited as long as the solvent has no toxicity to the cell and does not do harm to proliferative properties or functions of the cell. For example, water, a buffer, a cell culture medium and the like may be used. Examples of the buffer include phosphoric acid physiological saline (PBS), HEPES buffer, Hanks buffer and the like. Examples of the culture medium include D-MEM, E-MEM, MEMα, RPMI-1640, Ham's F-12, and the like.

An amount of the promoter mixed with the cell sample may be an amount sufficient for obtaining an effect of promoting spheroid formation, and can be optionally set depending on the kind of the cells in the mixture of the cell sample and the promoter, the number of constituent cells, and the culture environment. For example, the amount of the promoter mixed with the cell sample is preferably an amount such that the concentration of the promoter in the mixture of the cell sample and the promoter is 0.01 to 10 mg/mL, and more preferably an amount such that the concentration of the promoter in the mixture of the cell sample and the promoter is 0.1 to 1 mg/mL. When the concentration of the promoter in the mixture is within the range, the cells and the promoter in the mixture easily come into contact with each other, and as a result of the promoter being adhered onto the surface of a lot of cells, the effect of promoting spheroid formation is sufficiently obtained.

The promoter may be mixed with the cell sample in a state of solid such as powder. However, the promoter is preferably mixed with the cell sample in a state of being dissolved or suspended in a solvent. As the solvent in which the promoter is dissolved or suspended, the same solvent as the solvent for preparing a cell suspension may be used.

In the method of promoting spheroid formation according to the embodiment, the step (2) may be performed, after repeating the step (1) a plurality of times. That is, in the step (1), mixing of the cell sample with the promoter may be performed a plurality of times.

After the step (1), as the step (2), the mixture obtained in the step (1) is cultured inside a spheroid formation-culture vessel. By culturing the mixture inside the spheroid formation-culture vessel, a spheroid is formed in a fast manner due to action of the promoter adhered onto the surface of the cell. Preparation of the mixture in the step (1) may be performed inside the spheroid formation-culture vessel. Or after performing preparation inside another vessel, the step (2) may be performed by putting the obtained mixture inside the spheroid formation-culture vessel.

The spheroid formation-culture vessel used in the embodiment may be a vessel in which adhesion other than cell-cell adhesion is suppressed, or may be a vessel used for cell culture by a general spheroid culture method. Examples of the vessel include a culture vessel coated with functional molecules for realizing non-adhesive scaffold, a culture vessel with a cell non-adhesive gel attached on the surface thereof, a culture vessel in a micro liquid used in a micro liquid culture method (microdroplet culture method), and the like, for example. Examples of the material of the spheroid formation-culture vessel include glass, stainless steel, plastic, and the like, but are not limited thereto. Examples of the spheroid formation-culture vessel include dish, tube, flask, bottle, plate, and the like, but are not limited thereto.

Culture conditions inside the spheroid formation-culture vessel may be an environment suitable for the kind of used cell. For example, a culture medium recommended in culture of the kind of used cell may be used, and a temperature condition recommended in culture of the kind of used cell and the like may be set. In addition, the culture time may be also optionally set depending on the kind of used cell the number of the cells, and the size of the spheroid to be achieved.

For example, pellets of a cancer cell derived from a human are mixed with a solution containing heparin to prepare a suspension, the cancer cell and the heparin are brought into contact in the suspension, and the heparin is adhered on the cell surface. Subsequently, the suspension containing the cell on which the heparin is adhered is added to a culture vessel in a micro liquid in a specified amount, and held for an optional time in an environment suitable for cancer cell culture, for example, in an environment of 5% $CO_2$ gas and 37° C. With this, spheroid formation can be achieved in a fast manner. In the suspension, components which serve as an environment suitable for cell culture such as culture medium may be preferably included.

In the method of promoting spheroid formation according to the embodiment, before the step (2), external force is preferably applied to the cells in the mixture obtained in the step (1). Due to the external force, cells widely spread in the mixture are gathered in a certain region and the distance between the cells becomes short. As a result, it is possible to form a spheroid in a faster manner. The external force is not particularly limited as long as the external force acts such that the cells in the mixture move in a certain direction. Examples of the external force include centrifugal force, pressure, magnetic force, and the like.

The condition under which centrifugal force and pressure are applied may be a condition under which cells are gathered in a certain region while maintaining a state of the cells in the spheroid formation-culture vessel, and may be optionally set depending on the kind of used cell, the number of the cells, and the size of the spheroid to be achieved. In a case of the centrifugal force, for example, the centrifugal force may be sufficiently applied to a well plate kind culture vessel for an optional time with a centrifugal device. In addition, in a case of the pressure, for example, the pressure may be sufficiently applied to a well plate kind culture vessel with a pressurization kind or decompression kind device. In addition, in a case of using magnetic force, for example, it is possible to perform a method for forming a cell-magnetic body complex by using a magnetic body having a structure or function capable of specifically binding or being adhered to a cell, and gathering the complex on a bottom surface of a spheroid formation-culture vessel by using magnetic force.

For example, pellets of a cancer cell derived from a human is mixed with a solution containing heparin to prepare a suspension, the cancer cell d the heparin are brought into contact in the suspension, and the heparin is adhered on the cell surface. Subsequently, the suspension containing the cell on which the heparin is adhered is added to a culture vessel having a surface with low cell adhesiveness in a specified amount, and external force is applied thereto. After that, the suspension is held for an optional time in an environment suitable for cancer cell culture, for example, in an environment of 5% $CO_2$ gas and 37° C. With this, spheroid formation can be achieved in a fast manner. In the suspension, components which serve as an environment suitable for cell culture such as culture medium may be preferably included.

A kit for promoting spheroid formation according to an embodiment of the present invention includes the promoter.

The kit has preferably a configuration including the spheroid formation-culture vessel. In addition, the kit may include a buffer for preparing a cell suspension, a cell culture medium, and the like. In this manner, by making a reagent and the like required for the method of promoting spheroid formation according to an embodiment of the present invention into a kit, it is possible to perform spheroid formation more conveniently in a shorter time.

EXAMPLES

Hereinafter, a detailed description will be provided on the present invention with reference to Examples, but the present invention is not limited to the following examples.

Example 1

A spheroid formed from one kind of cell was formed.

As the cells, two kinds of cells, that is, a human colon adenocarcinoma cell line HT29 (HTB-38 (registered trademark) of ATCC (American Type Culture Collection)) as a cell for easily forming a spheroid, and a human mammary gland cancer cell line MCF7 (HTB-22 (registered trademark) of ATCC) as a cell for hardly forming a spheroid were used. As the culture vessel, PERFECTA 3D Biomatrix Hanging Drop Plate (manufactured by 3D Biomatrix corporation, NT-HDP1096) which is a culture vessel in a micro liquid was used. As the culture medium, a serum culture medium in which 10 vol/vol % bovine serum (manufactured by Corning Inc., #35-010-01) and 1 vol/vol % penicillin/streptomycin (manufactured by Waco Pure Chemical Industries, Ltd., 168-23191) are contained in D-MEM (manufactured by Waco Pure Chemical Industries, Ltd., 043-30085) was used. As the promoter, heparin (manufactured by SIGMA Corporation. H3149) was used.

Specifically, first, regarding each cell, cells and heparin were added to a serum culture medium and mixed with each other such that a concentration of heparin is 1 mg/mL, and a concentration of the cells is $1\times10^4$ cells/50 µL to prepare a cell suspension.

Subsequently, the prepared cell suspension was added to each of three wells of a culture vessel in a micro liquid in an amount of 50 µL per well (number of cells per well is $1\times10^4$ cells), cultured for 72 hours in an environment of 37° C. and 5% $CO_2$ gas, and presence or absence of spheroid formation was evaluated over time. In addition, the survival rate of the cells after culture for 72 hours was examined. For comparison, the same operation was carried out under a condition in which a promoter was absent.

For the evaluation of spheroid formation, image analysis was performed on the cell suspension by direct observation using an inverted type microscope at 10 points of 2, 4, 6, 8, 10, 12, 18, 24, 48, and 72 hours from start of culture, and evaluation was carried out into three stages. The evaluation value 1 indicates absence of spheroid formation (a suspended state), the evaluation value 2 indicates a sign of spheroid formation (a non-uniform aggregate such as an island-shaped aggregate is formed), and the evaluation value 3 indicates presence of spheroid formation (a uniform spheroid in a spherical shape is formed). The evaluation method was the same in each of Examples.

Regarding the survival rates of the cells, analysis of the number of living cells was performed. Specifically, a trepan blue solution was added to the cell suspension after culture for 72 hours, and the number of stained cells was counted by using a cell counter (Countess II) manufactured by Life Technologies for evaluation.

Regarding each cell, the result of evaluation of spheroid formation for each well ("N1", "N2", and "N3") is shown in Table 1. In addition, the average values of three wells regarding the number of the living cells and the survival rates (%) obtained by the analysis of the number of the living cells are shown in Table 2.

TABLE 1

| Culture Time | MCF7 | | | | | | HT29 | | | | | |
|---|---|---|---|---|---|---|---|---|---|---|---|---|
| | Promoter absent | | | Promoter present | | | Promoter absent | | | Promoter present | | |
| (time) | N1 | N2 | N3 | N1 | N2 | N3 | N1 | N2 | N3 | N1 | N2 | N3 |
| 2 | 1 | 1 | 1 | 1 | 1 | 1 | 1 | 1 | 1 | 1 | 1 | 1 |
| 4 | 1 | 1 | 1 | 1 | 1 | 1 | 1 | 1 | 1 | 2 | 2 | 2 |
| 6 | 1 | 1 | 1 | 1 | 1 | 1 | 1 | 1 | 1 | 3 | 2 | 2 |
| 8 | 1 | 1 | 1 | 1 | 1 | 1 | 1 | 1 | 1 | 3 | 3 | 3 |
| 10 | 1 | 1 | 1 | 2 | 1 | 1 | 1 | 1 | 1 | 3 | 3 | 3 |
| 12 | 1 | 1 | 1 | 2 | 2 | 2 | 2 | 2 | 1 | 3 | 3 | 3 |
| 18 | 1 | 1 | 1 | 2 | 2 | 2 | 2 | 2 | 2 | 3 | 3 | 3 |
| 24 | 1 | 1 | 1 | 2 | 2 | 2 | 2 | 2 | 2 | 3 | 3 | 3 |
| 48 | 1 | 2 | 1 | 2 | 2 | 2 | 3 | 2 | 3 | 3 | 3 | 3 |
| 72 | 2 | 2 | 2 | 3 | 3 | 2 | 3 | 3 | 3 | 3 | 3 | 3 |

TABLE 2

| | MCF7 | | HT29 | |
|---|---|---|---|---|
| | Promoter absent | Promoter present | Promoter absent | Promoter present |
| Number of living cells ($\times10^5$ cells) | 1.7 ± 0.7 | 1.8 ± 0.4 | 0.9 ± 0.3 | 1.1 ± 0.2 |
| Survival rate (%) | 83 ± 3 | 89 ± 1 | 79 ± 4 | 80 ± 2 |

As shown in Table 1, in a case of the MCF7 cells, in the cell suspension in which a promoter was absent, the cells did not reach the evaluation value 3 even after culture for 72 hours, whereas in the cell suspension in which a promoter was present, the cells reached the evaluation value 3 in two wells among the three wells after culture for 72 hours. In addition, in a case of the HT29 cells, it took 48 to 72 hours until the cells reached the evaluation value 3 in the cell suspension in which a promoter was absent, whereas it took 6 to 8 hours cells reached the evaluation value 3 in the cell suspension in which a promoter was present. Thus, it was possible to shorten the spheroid formation time by about ⅛.

On the other hand, as shown in Table 2, the survival rates of both cells were at the similar degrees in any of the case where a promoter was absent and the case where a promoter was present. Therefore, it was acknowledged that the promoter does not do harm to survivability of the cells.

Figure 1:
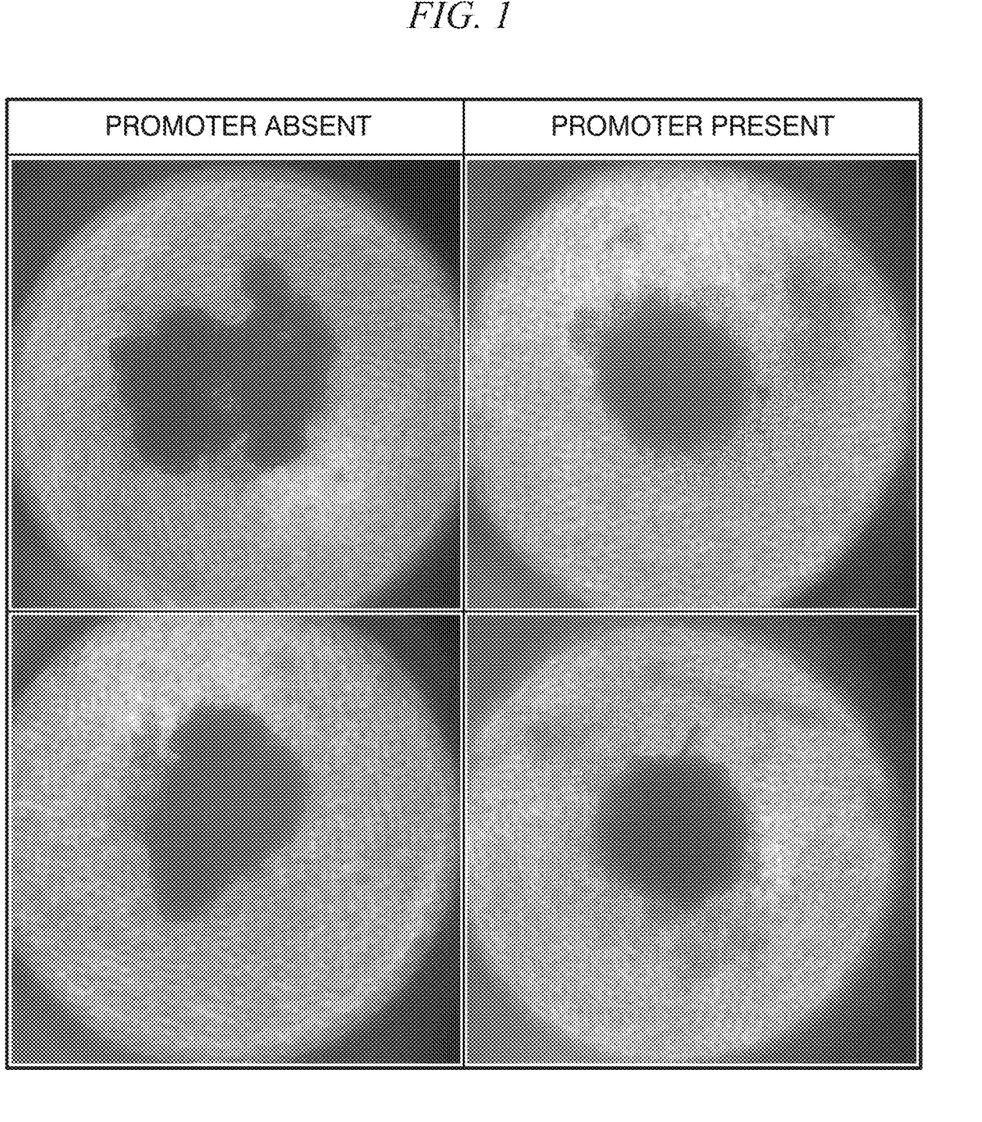
FIG. 1 is a photograph of transmitted light of a spheroid of HT29 cells formed after culture for 24 hours in Example 1.

In addition, FIG. 1 shows a photograph of transmitted light of a spheroid formed after culture for 24 hours in the HT29 cells. In FIG. 1, two figures on the left side show a spheroid (upper figure: N1 well, lower figure: N2 well) observed in the cell suspension in which a promoter is absent, and two figures on the right side show a spheroid (upper figure: N1 well, lower figure: N2 well) observed in the cell suspension in which a promoter is present.

As shown in FIG. 1, most spheroids observed in the cell suspension in which a promoter is absent have a distorted shape. Whereas spheroids observed in the cell suspension in Which a promoter is present are spherical and have similar sizes and the formed spheroids have relatively homogenous shapes and sizes.

Example 2

A spheroid formed from three kinds of cells was formed.

As the cells, three kinds of cells, that is, HT29 cells used in Example 1 as well, skin fibroblasts derived from a human newborn (manufactured by Lonza. Group, CC-2509 Normal Human Dermal Fibroblasts: NHDF), and human umbilical vein endothelial cells (manufactured by Lonza Group, CC-2517A Human Umbilical Vein Endothelial Cell: HUVEC) were used.

Specifically, in the same manner as in Example 1 except that a cell mixture obtained by mixing HT29 cells, NHDF cells, and HUVEC cells at 20,000: 12,000: 8,000 (number of cells) was used as the cells, a cell suspension to which heparin was mixed was prepared, and cultured in a culture vessel in a micro liquid for 72 hours. In addition, in the same manner as in Example 1, spheroid formation in the cell suspension was evaluated over time, and survival rates of the cells after culture for 72 hours was examined. For comparison, the same operation was carried out under a condition in which a promoter was absent.

The result of evaluation of spheroid formation for each well ("N1", "N2", and "N3") is shown in Table 3. In addition, the average values of three wells regarding the number of the living cells and the survival rates (%) obtained by the analysis of the number of the living cells are shown in Table 4.

TABLE 3

| Culture time (time) | HT29-HUVEC-NHDF | | | | | |
|---|---|---|---|---|---|---|
| | Promoter absent | | | Promoter present | | |
| | N1 | N2 | N3 | N1 | N2 | N3 |
| 2 | 1 | 1 | 1 | 1 | 1 | 1 |
| 4 | 1 | 1 | 1 | 1 | 1 | 1 |
| 6 | 1 | 1 | 1 | 1 | 2 | 2 |
| 8 | 1 | 1 | 1 | 1 | 2 | 2 |
| 10 | 1 | 1 | 1 | 2 | 2 | 2 |
| 12 | 2 | 2 | 1 | 2 | 2 | 2 |
| 18 | 2 | 2 | 2 | 2 | 3 | 3 |
| 24 | 2 | 2 | 2 | 3 | 3 | 3 |
| 48 | 2 | 2 | 2 | 3 | 3 | 3 |
| 72 | 2 | 2 | 2 | 3 | 3 | 3 |

TABLE 4

| | HT29-HUVEC-NHDF | |
|---|---|---|
| | Promoter absent | Promoter present |
| Number of living cells ($\times 10^5$ cells) | 0.6 ± 0.1 | 0.9 ± 0.4 |
| Survival rate (%) | 52 ± 3 | 76 ± 2 |

As shown in Table 3, in the cell suspension in which a promoter was absent, the cells did not reach the evaluation value 3 even after culture for 72 hours, whereas in the cell suspension in which a promoter was present, the cells reached the evaluation value 3 in all of the three wells after culture for 24 hours. In addition, as shown in Table 4, compared to the case where a promoter was absent, the number of the living cells was about 1.5 times, and the survival rate was about 1.5 times, in the case where a promoter was present.

Figure 2:
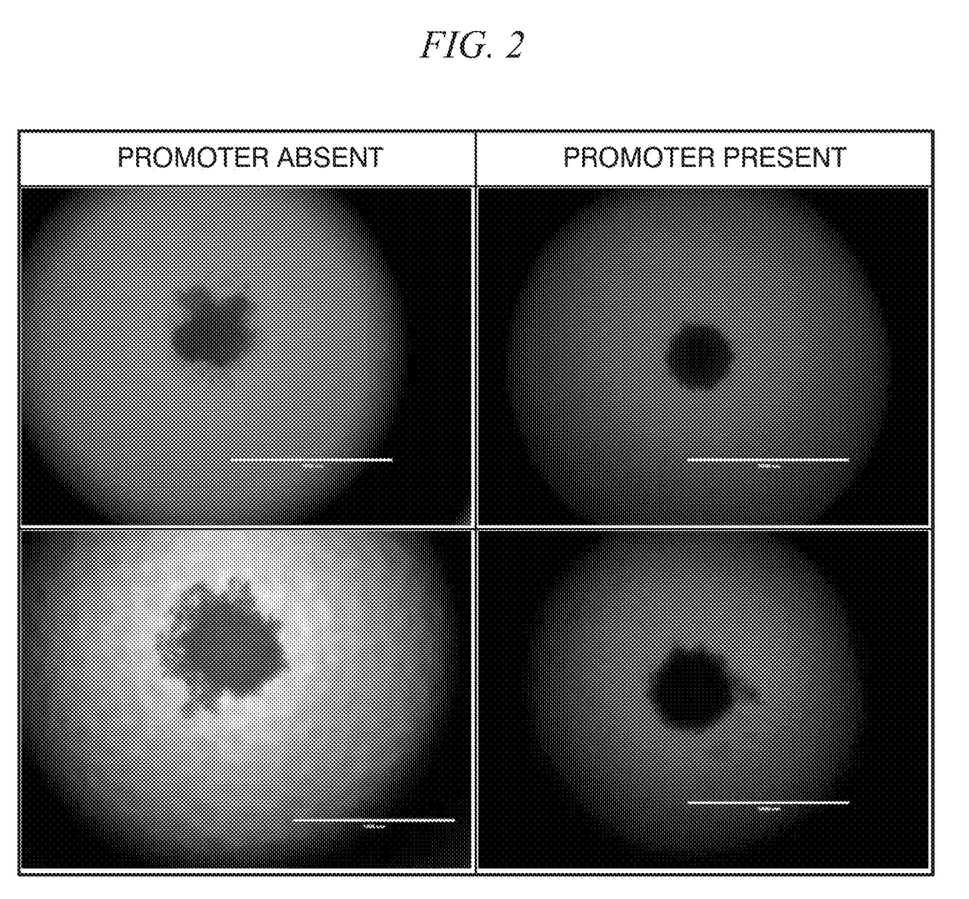
FIG. 2 is a photograph of transmitted light of a spheroid formed after culture for 24 hours in Example 2.

In addition, FIG. 2 shows a photograph of transmitted light of a spheroid formed after culture for 24 hours.

In FIG. 2, two figures on the left side show a spheroid observed in the cell suspension in which a promoter is absent, and two figures on the right side show a spheroid observed in the cell suspension in which a promoter is present. As shown in FIG. 2, most spheroids observed in the cell suspension in which a promoter is absent have a distorted shape, whereas spheroids observed in the cell suspension in which a promoter is present are spherical and have similar sizes and the formed spheroids have relatively homogenous shapes and sizes.

Example 3

Under a condition in which external force is applied after addition of a promoter and before culture, a spheroid formed from one kind of cell was formed.

As the cells, MCF7 used in Example 1 as well was used. As the culture vessel, a low cell adsorption plate GravityTRAP (registered trademark) ULA Plate (manufactured by Insphero Inc., ISP-09-001) was used. As the culture medium, the serum, culture medium used in Example 1 as well was used, and as the promoter, heparin used in Example 1 as well was used.

Specifically, first, in the same manner as in Example 1, heparin and the cells were mixed with a serum culture medium to prepare a cell suspension. Subsequently, the prepared cell suspension was added to each of three wells of a low cell adsorption plate in an amount of 50 μL per well (number of cells per well is $1 \times 10^4$ cells), and then the low cell adsorption plate was subjected to centrifugal treatment for one minute at 400×g. After that, the low cell adsorption plate was cultured for 72 hours in an environment of 37° C. and 5% $CO_2$ gas. In addition, in the same manner as in Example 1, spheroid formation in the cell suspension was evaluated over time, and the survival rate of the cells after culture for 72 hours was examined. For comparison, the same operations were carried out under a condition in which a promoter was absent and centrifugal treatment was also not performed and a condition in which a promoter was present but a centrifugal treatment was not performed.

The result of evaluation of spheroid formation for each well ("N1", "N2", and "N3") is shown in Table 5. In addition, the average values of three wells regarding the number of the living cells and the survival rates (%) obtained by the analysis of the number of the living cells are shown in Table 6. In Tables 5 and 6, "promoter absent" indicates the result obtained under the condition in which a promoter was absent and centrifugal treatment was also not performed, "promoter present" indicates the result obtained under the condition in which a promoter was present but centrifugal treatment was not performed, and "promoter/external force present" indicates the result obtained under the condition in which a promoter was present and centrifugal treatment was also performed, respectively.

TABLE 5

| Culture time | MCF7 | | | | | | | | |
| --- | --- | --- | --- | --- | --- | --- | --- | --- | --- |
| | Promoter absent | | | Promoter present | | | Promoter/external force present | | |
| (time) | N1 | N2 | N3 | N1 | N2 | N3 | N1 | N2 | N3 |
| 2 | 1 | 1 | 1 | 1 | 1 | 1 | 2 | 2 | 2 |
| 4 | 1 | 1 | 1 | 1 | 1 | 1 | 2 | 2 | 2 |
| 6 | 1 | 1 | 1 | 1 | 1 | 1 | 2 | 2 | 2 |
| 8 | 1 | 1 | 1 | 1 | 1 | 1 | 2 | 2 | 2 |
| 10 | 1 | 1 | 1 | 2 | 1 | 1 | 3 | 3 | 3 |
| 12 | 1 | 1 | 1 | 2 | 2 | 2 | 3 | 3 | 3 |
| 18 | 1 | 1 | 1 | 2 | 2 | 2 | 3 | 3 | 3 |
| 24 | 1 | 1 | 1 | 2 | 2 | 2 | 3 | 3 | 3 |
| 48 | 1 | 2 | 1 | 2 | 2 | 2 | 3 | 3 | 3 |
| 72 | 2 | 2 | 2 | 3 | 3 | 2 | 3 | 3 | 3 |

TABLE 6

| | MCF7 | | |
| --- | --- | --- | --- |
| | Promoter absent | Promoter present | Promoter/external force present |
| Number of living cells ($\times 10^5$ cells) | 1.7 ± 0.7 | 1.8 ± 0.4 | 1.7 ± 0.6 |
| Survival rate (%) | 83 ± 3 | 89 ± 1 | 85 ± 2 |

As shown in Table 5, in the cell suspension in which a promoter was absent, the cells did not reach the evaluation value 3 even after culture for 72 hours, and in the cell suspension in which a promoter was present, the cells reached the evaluation value 3 in two wells among the three wells only after culture for 72 hours. On the contrary, in the cell suspension in which a promoter was present and external force was applied before culture, the cells reached the evaluation value 3 in all of the three wells after culture for 10 hours. From the result, it was recognized that by applying external force to the cell suspension before culture of cells, spheroid formation is further promoted. On the other hand, as shown in Table 6, the survival rates of the cells were at the similar degrees in any of the conditions. Therefore, it was acknowledged that addition of the promoter or external force does not do harm to survivability of the cells.

Example 4

Under a condition in which external force was applied after addition of a promoter and before culture, a spheroid formed from three kinds of cells was formed.

As the cells, HT29 cells, NHDF cells, and HUVEC cells used in Example 2 as well were used. As the culture vessel, the low cell adsorption plate used in Example 3 as well was used. As the culture medium, the serum culture medium used in Example 1 as well was used. As the promoter, heparin used in Example 1 as well was used.

Specifically, in the same manner as in Example 3 except that a cell mixture obtained by mixing HT29 cells, NHDF cells, and HUVEC cells at 20,000: 12,000: 8,000 (number of cells) was used as the cells, a cell suspension to which heparin was mixed was prepared, and added to a well of the low cell adsorption plate. After that, in the same manner as in Example 3, the low cell adsorption plate was subjected to centrifugal treatment and cultured for 72 hours. In addition, in the same manner as in Example 1, spheroid formation in the cell suspension was evaluated over time, and the survival rate of the cells after culture for 72 hours was examined. For comparison, the same operation was carried out under a condition in which a promoter was absent and centrifugal treatment was also not performed and a condition in which a promoter was present but centrifugal treatment was not performed.

The result of evaluation of spheroid formation for each well ("N1", "N2", and "N3") is shown in Table 7. In addition, the average values of three wells regarding the number of the living cells and the survival rates (%) obtained by the analysis of the number of the living cells are shown in Table 8. In Tables 7 and 8, "promoter absent", "promoter present", and "promoter/external force present" indicate the same as in Table 5.

TABLE 7

| Culture time | HT29-HUVEC-NHDF | | | | | | | | |
| --- | --- | --- | --- | --- | --- | --- | --- | --- | --- |
| | Promoter absent | | | Promoter present | | | Promoter/external force present | | |
| (time) | N1 | N2 | N3 | N1 | N2 | N3 | N1 | N2 | N3 |
| 2 | 1 | 1 | 1 | 1 | 1 | 1 | 2 | 2 | 2 |
| 4 | 1 | 1 | 1 | 1 | 1 | 1 | 2 | 2 | 2 |
| 6 | 1 | 1 | 1 | 1 | 2 | 2 | 2 | 2 | 2 |
| 8 | 1 | 1 | 1 | 1 | 2 | 2 | 3 | 2 | 3 |
| 10 | 1 | 1 | 1 | 2 | 2 | 2 | 3 | 3 | 3 |
| 12 | 2 | 2 | 1 | 2 | 2 | 2 | 3 | 3 | 3 |
| 18 | 2 | 2 | 2 | 2 | 3 | 3 | 3 | 3 | 3 |
| 24 | 2 | 2 | 2 | 3 | 3 | 3 | 3 | 3 | 3 |
| 48 | 2 | 2 | 2 | 3 | 3 | 3 | 3 | 3 | 3 |
| 72 | 2 | 2 | 2 | 3 | 3 | 3 | 3 | 3 | 3 |

TABLE 8

| | HT29-HUVEC-NHDF | | |
| --- | --- | --- | --- |
| | Promoter absent | Promoter present | Promoter/external force present |
| Number of living cells ($\times 10^5$ cells) | 0.6 ± 0.1 | 0.9 ± 0.4 | 1.1 ± 0.3 |
| Survival rate (%) | 52 ± 3 | 76 ± 2 | 75 ± 4 |

As shown in Table 7, in the cell suspension in which a promoter was absent, the cells did not reach the evaluation value 3 even after culture for 72 hours, and in the cell suspension in which a promoter was present, the cells reached the evaluation value 3 in two wells among the three wells only after culture for 24 hours. On the contrary, in the cell suspension in which a promoter was added and external force was applied before culture, the cells reached the evaluation value 3 in all of the three wells after culture for 10 hours. From the result, it was recognized that even in a case of forming a spheroid from a plurality of kinds of cells, by applying external force to the cell suspension before culture of cells, spheroid formation is further promoted. On the other hand, as shown in Table 8, the survival rates of the cells in the case where a promoter was added and external force was applied before culture were almost the same as the survival rates of the cells in the case where a promoter was added and external force was not applied before culture. Therefore, it was acknowledged that the addition of external force performed in this example does not do harm to survivability of the cells.

Example 5

By using three kinds of glycosaminoglycan as the promoter, a spheroid was formed.

As the cells, MCF7 used in Example 1 was used. As the culture vessel, the low cell adsorption plate used in Example 3 as well was used. As the culture medium, the serum culture medium used in Example 1 as well was used. As the promoter, heparin used in Example 1 as well, sodium chondroitin sulfate (manufactured by SIGMA Corporation, C3788), and sodium hyaluronate (manufactured by SIGMA Corporation, H1876) were used.

Specifically, first, in the same manner as in Example 1, each of the promoters was added to the cells to prepare a cell suspension in which a concentration of heparin was 1 mg/mL and a concentration of cells is $1 \times 10^4$ cells/50 µL, a cell suspension in which a concentration of sodium chondroitin sulfate was 1 mg/mL and a concentration of cells is $1 \times 10^4$ cells/50 µL, and a cell suspension in which a concentration of sodium hyaluronate was 1 mg/mL, and a concentration of cells was $1 \times 10^4$ cells/50 µL, respectively. Subsequently, in the same manner as in Example 3, each of the cell suspensions was added to each of the wells of the low cell adsorption plate, and then the low cell adsorption plate was subjected to centrifugal treatment and cultured for 72 hours. In addition, in the same manner as in Example 1, spheroid formation in the cell suspensions was evaluated over time, and survival rates of the cells after culture for 72 hours were examined. For comparison, the same operation was carried out under a condition in which a promoter was absent and centrifugal treatment was also not performed.

Regarding each of the cell suspensions in which each of the promoters was added, the result of evaluation of spheroid formation for each well ("N1", "N2", and "N3") is shown in Table 9. In addition, the average values of three wells regarding the number of the living cells and the survival rates (%) obtained by the analysis of the number of the living cells are shown in Table 10. In Tables 9 and 10, "chondroitin" indicates the result of the cell suspension in which sodium chondroitin sulfate was added, and "hyaluron" indicates the result of the cell suspension in which sodium hyaluronate was added, respectively.

TABLE 9

| | MCF7 | | | | | | | | | | | |
|---|---|---|---|---|---|---|---|---|---|---|---|---|
| | Promoter absent | | | Heparin | | | Chondroitin | | | Hyaluron | | |
| | N1 | N2 | N3 | N1 | N2 | N3 | N1 | N2 | N3 | N1 | N2 | N3 |
| 2 | 1 | 1 | 1 | 2 | 2 | 2 | 2 | 2 | 2 | 2 | 2 | 2 |
| 4 | 1 | 1 | 1 | 2 | 2 | 2 | 2 | 2 | 2 | 2 | 2 | 2 |
| 6 | 1 | 1 | 1 | 2 | 2 | 2 | 2 | 2 | 2 | 2 | 2 | 2 |
| 8 | 1 | 1 | 1 | 3 | 2 | 3 | 2 | 2 | 2 | 2 | 2 | 2 |
| 10 | 1 | 1 | 1 | 3 | 3 | 3 | 2 | 2 | 2 | 2 | 2 | 2 |
| 12 | 1 | 1 | 1 | 3 | 3 | 3 | 2 | 2 | 2 | 2 | 2 | 2 |
| 18 | 1 | 1 | 1 | 3 | 3 | 3 | 2 | 2 | 2 | 2 | 2 | 2 |
| 24 | 1 | 1 | 1 | 3 | 3 | 3 | 2 | 2 | 2 | 2 | 2 | 2 |
| 48 | 1 | 2 | 1 | 3 | 3 | 3 | 3 | 2 | 2 | 2 | 2 | 2 |
| 72 | 2 | 2 | 2 | 3 | 3 | 3 | 3 | 3 | 3 | 2 | 3 | 3 |

TABLE 10

| | MCF7 | | | |
|---|---|---|---|---|
| | Promoter absent | Heparin | Chondroitin | Hyaluron |
| Number of living cells ($\times 10^5$ cells) | 1.7 ± 0.7 | 1.7 ± 0.6 | 1.8 ± 0.3 | 1.6 ± 0.5 |
| Survival rate (%) | 83 ± 3 | 85 ± 2 | 84 ± 1 | 86 ± 2 |

As shown in Table 9, in the cell suspension in which a promoter was absent, the cells did not reach the evaluation value 3 even after culture for 72 hours, whereas in the cell suspension in which heparin was added, the cells reached the evaluation value 3 in all of the three wells after culture for 10 hours. In the cell suspension in which sodium chondroitin sulfate was added, the cells reached the evaluation value 3 in all of the three wells after culture for 72 hours, and in the cell suspension in which sodium hyaluronate was added, the cells reached the evaluation value 3 in two wells among the three wells after culture for 72 hours. From the result, it was recognized that in the case of chondroitin sulfate and hyaluronic acid, the same effect of promoting spheroid formation as that of the case of heparin was obtained. In addition, as shown in Table 10, the survival rates of the cells were at the similar degrees in any of the cell suspensions. Therefore, it was acknowledged that addition of the promoter does not do harm to the survivability of the cells.

Example 6

An effect of a concentration of a promoter in a cell suspension on spheroid formation was examined. As the cells, MCF7 used in Example 1 as well was used. As the culture vessel, the low cell adsorption plate used in Example 3 as well was used. As the culture medium, the serum culture medium used in Example 1 as well seas rued. As the promoter, heparin used in Example 1 as well was used.

Specifically, in the same manner as in Example 3 except that heparin was added such that a final concentration of heparin in the cell suspension was 0.01, 0.1, 1, and 10 mg/mL, a cell suspension to which heparin was mixed was prepared, and added to a well of the low cell adsorption plate. After that, in the same manner as in Example 3, the low cell adsorption plate was subjected to centrifugal treatment and cultured for 72 hours. In addition, in the same manner as in Example 1, spheroid formation in the cell suspension was evaluated over time, and the survival rate of the cells after culture for 72 hours was examined. For comparison, the same operation was carried out under a condition in which a promoter was absent and centrifugal treatment was also not performed.

Regarding each of the cell suspensions, the results of evaluation of spheroid formation for each well ("N1", "N2", and "N3") are shown in Tables 11 and 12. In addition, the average values of three wells regarding the number of the living cells and the survival rates (%) obtained by the analysis of the number of the living cells are shown in Table 13. In Tables 11 to 13, "0.01 mg/mL" "0.1 mg/mL", "1 mg/mL", and "10 mg/mL" indicate the result of the cell suspension in which heparin was contained to be 0.01 mg/mL, the result of the cell suspension in which heparin was contained to be 0.1 mg/mL, the result of the cell suspension in which heparin was contained to be 1 mg/mL, and the result of the cell suspension in which heparin was contained to be 10 mg/mL, respectively.

TABLE 11

| Culture time | MCF7 | | | | | | | | |
|---|---|---|---|---|---|---|---|---|---|
| | Promoter absent | | | 0.01 mg/mL | | | 0.1 mg/mL | | |
| (time) | N1 | N2 | N3 | N1 | N2 | N3 | N1 | N2 | N3 |
| 2 | 1 | 1 | 1 | 1 | 2 | 1 | 2 | 2 | 2 |
| 4 | 1 | 1 | 1 | 2 | 2 | 2 | 2 | 2 | 2 |
| 6 | 1 | 1 | 1 | 2 | 2 | 2 | 2 | 2 | 2 |
| 8 | 1 | 1 | 1 | 2 | 2 | 2 | 2 | 3 | 2 |
| 10 | 1 | 1 | 1 | 2 | 2 | 2 | 3 | 3 | 3 |
| 12 | 1 | 1 | 1 | 2 | 2 | 2 | 3 | 3 | 3 |
| 18 | 1 | 1 | 1 | 2 | 2 | 3 | 3 | 3 | 3 |
| 24 | 1 | 1 | 1 | 3 | 3 | 3 | 3 | 3 | 3 |
| 48 | 1 | 2 | 1 | 3 | 3 | 3 | 3 | 3 | 3 |
| 72 | 2 | 2 | 2 | 3 | 3 | 3 | 3 | 3 | 3 |

TABLE 12

| Culture time | MCF7 | | | | | |
|---|---|---|---|---|---|---|
| | 1 mg/mL | | | 10 mg/mL | | |
| (time) | N1 | N2 | N3 | N1 | N2 | N3 |
| 2 | 2 | 2 | 2 | 2 | 2 | 2 |
| 4 | 2 | 2 | 2 | 2 | 2 | 2 |
| 6 | 2 | 2 | 2 | 2 | 2 | 2 |
| 8 | 3 | 2 | 3 | 2 | 2 | 2 |
| 10 | 3 | 3 | 3 | 2 | 2 | 2 |
| 12 | 3 | 3 | 3 | 3 | 2 | 3 |
| 18 | 3 | 3 | 3 | 3 | 3 | 3 |
| 24 | 3 | 3 | 3 | 3 | 3 | 3 |
| 48 | 3 | 3 | 3 | 3 | 3 | 3 |
| 72 | 3 | 3 | 3 | 3 | 3 | 3 |

TABLE 13

| | MCF7 | | | | |
|---|---|---|---|---|---|
| | Promoter absent | 0.01 mg/mL | 0.1 mg/mL | 1 mg/mL | 10 mg/mL |
| Number of living cells ($\times 10^5$ cells) | 1.7 ± 0.7 | 1.6 ± 0.3 | 1.7 ± 0.9 | 1.7 ± 0.6 | 1.6 ± 0.5 |
| Survival rate (%) | 83 ± 3 | 83 ± 2 | 87 ± 1 | 85 ± 2 | 82 ± 6 |

As shown in Tables 11 and 12, in the cell suspension in which a promoter was absent, the cells did not reach the evaluation value 3 even after culture for 72 hours, whereas in the cell suspension in which 0.01 mg/mL of heparin was added, the cells reached the evaluation value 3 in all of the wells after culture for 24 hours. In the cell suspension in which 0.01 mg/nit, of heparin was added and in the cell suspension in which 1 mg/mL, of heparin was added, the cells reached the evaluation value 3 in all of the wells after culture for I0 hours. In the cell suspension in which 10 mg/mL of heparin was added, the cells reached the evaluation value 3 in all of the wells after culture for 18 hours. In addition, as shown in Table 13, the survival rates of the cells were the same in any of the cell suspensions.

Example 7

The effect of the number of the cells in the cell suspension on spheroid formation was examined.

As the cells, MCF7 used in Example 1 as well was used. As the culture vessel, the low cell adsorption plate used in Example 3 as well was used. As the culture medium, the serum culture medium used in Example 1 as well was used. As the promoter, heparin used in Example 1 as well was used.

Specifically, in the same manner as in Example 3 except that cell suspensions were prepared such that the numbers of the cells are $1\times10^3$ cells/50 μL, $1\times10^4$ cells/50 μL, $1\times10^5$ cells/50 μL, and $1\times10^6$ cells/50 μL, cell suspensions to which heparin was mixed were prepared, and added to a well of the low cell adsorption plate. After that, in the same manner as in Example 3, the low cell adsorption plate was subjected to centrifugal treatment and cultured for 72 hours. In addition, in the same manner as in Example 1, spheroid formation in the cell suspensions was evaluated over time, and the survival rate of the cells after culture for 72 hours was examined. For comparison, the same operation was carried out under a condition in which a promoter was absent and centrifugal treatment was also not performed.

Regarding each of the cell suspensions, the results of evaluation of spheroid formation for each well ("N1", "N2", and "N3") are shown in Tables 14 and 15. In addition, the average values of three wells regarding the number of the living cells and the survival rates (%) obtained by the analysis of the number of the living cells are shown in Tables 16 and 17. In Tables 14 to 16, "$1\times10^3$ cells", "$1\times10^4$ cells", "$1\times10^5$ cells", and "$1\times10^6$ cells" indicate the result of the cell suspension in which the number of the cells is $1\times10^3$ cells/50 μL, the result of the cell suspension in which the number of the cells is $1\times10^4$ cells/50 μL, the result of the cell suspension in which the number of the cells is $1\times10^5$ cells/50 μL, and the result of the cell suspension in which the number of the cells is $1\times10^6$ cells/50 μL, respectively.

TABLE 14

| | $1 \times 10^3$ cells | | | | | | $1 \times 10^4$ cells | | | | | |
|---|---|---|---|---|---|---|---|---|---|---|---|---|
| Culture time | Promoter absent | | | Promoter present | | | Promoter absent | | | Promoter present | | |
| (time) | N1 | N2 | N3 | N1 | N2 | N3 | N1 | N2 | N3 | N1 | N2 | N3 |
| 2 | 1 | 1 | 1 | 2 | 2 | 2 | 1 | 1 | 1 | 2 | 2 | 2 |
| 4 | 1 | 1 | 1 | 2 | 2 | 2 | 1 | 1 | 1 | 2 | 2 | 2 |
| 6 | 1 | 1 | 1 | 2 | 2 | 2 | 1 | 1 | 1 | 2 | 2 | 2 |
| 8 | 1 | 1 | 1 | 2 | 3 | 3 | 1 | 1 | 1 | 3 | 2 | 3 |
| 10 | 1 | 1 | 1 | 3 | 3 | 3 | 1 | 1 | 1 | 3 | 3 | 3 |
| 12 | 1 | 1 | 1 | 3 | 3 | 3 | 1 | 1 | 1 | 3 | 3 | 3 |
| 18 | 1 | 2 | 1 | 3 | 3 | 3 | 1 | 1 | 1 | 3 | 3 | 3 |
| 24 | 2 | 2 | 2 | 3 | 3 | 3 | 1 | 1 | 1 | 3 | 3 | 3 |
| 48 | 2 | 2 | 2 | 3 | 3 | 3 | 1 | 2 | 1 | 3 | 3 | 3 |
| 72 | 2 | 2 | 2 | 3 | 3 | 3 | 2 | 2 | 2 | 3 | 3 | 3 |

TABLE 15

| | $1 \times 10^5$ cells | | | | | | $1 \times 10^6$ cells | | | | | |
|---|---|---|---|---|---|---|---|---|---|---|---|---|
| Culture time | Promoter absent | | | Promoter present | | | Promoter absent | | | Promoter present | | |
| (time) | N1 | N2 | N3 | N1 | N2 | N3 | N1 | N2 | N3 | N1 | N2 | N3 |
| 2 | 1 | 1 | 1 | 2 | 2 | 2 | 1 | 1 | 1 | 2 | 2 | 2 |
| 4 | 1 | 1 | 1 | 2 | 2 | 2 | 1 | 1 | 1 | 2 | 2 | 2 |
| 6 | 1 | 1 | 1 | 2 | 2 | 2 | 1 | 1 | 1 | 2 | 2 | 2 |
| 8 | 1 | 1 | 1 | 2 | 2 | 2 | 1 | 1 | 1 | 2 | 2 | 2 |
| 10 | 1 | 1 | 1 | 2 | 2 | 3 | 1 | 1 | 1 | 2 | 2 | 2 |
| 12 | 1 | 1 | 1 | 2 | 3 | 3 | 1 | 1 | 1 | 2 | 2 | 2 |

TABLE 15-continued

| Culture time | 1 × 10⁵ cells | | | | | | 1 × 10⁶ cells | | | | | |
|---|---|---|---|---|---|---|---|---|---|---|---|---|
| | Promoter absent | | | Promoter present | | | Promoter absent | | | Promoter present | | |
| (time) | N1 | N2 | N3 | N1 | N2 | N3 | N1 | N2 | N3 | N1 | N2 | N3 |
| 18 | 1 | 1 | 1 | 3 | 3 | 3 | 1 | 1 | 1 | 2 | 2 | 2 |
| 24 | 1 | 1 | 1 | 3 | 3 | 3 | 1 | 1 | 1 | 2 | 3 | 2 |
| 48 | 1 | 1 | 1 | 3 | 3 | 3 | 1 | 1 | 1 | 3 | 3 | 3 |
| 72 | 2 | 2 | 2 | 3 | 3 | 3 | 2 | 1 | 2 | 3 | 3 | 3 |

TABLE 16

| | 1 × 10³ cells | | 1 × 10⁴ cells | |
|---|---|---|---|---|
| | Promoter absent | Promoter present | Promoter absent | Promoter present |
| Number of living cells (cells) | $4.3 \pm 0.5 \times 10^3$ | $5.5 \pm 0.8 \times 10^3$ | $1.7 \pm 0.7 \times 10^5$ | $1.7 \pm 0.6 \times 10^5$ |
| Survival rate (%) | 52 ± 3 | 72 ± 5 | 83 ± 3 | 85 ± 2 |

TABLE 17

| | 1 × 10⁵ cells | | 1 × 10⁶ cells | |
|---|---|---|---|---|
| | Promoter absent | Promoter present | Promoter absent | Promoter present |
| Number of living cells (cells) | $4.8 \pm 0.7 \times 10^5$ | $5.0 \pm 0.6 \times 10^5$ | $3.3 \pm 0.8 \times 10^6$ | $4.3 \pm 0.6 \times 10^6$ |
| Survival rate (%) | 67 ± 3 | 75 ± 4 | 48 ± 4 | 68 ± 5 |

As shown in Tables 14 and 15, in the cell suspension in which a promoter was absent, the cells did not reach the evaluation value 3 even after culture for 72 hours, whereas in the cell suspension in which heparin was added, the cells reached the evaluation value 3 in all of the wells after culture for 48 hours, regardless of the number of the cells. In particular, in the cell suspension in which the number of the cells was 1×10³ cells/50 μL and the cell suspension in which the number of the cells was 1×10⁴ cells/50 μL, the cells reached the evaluation value 3 in all of the wells after culture for 10 hours. In the cell suspension in which the number of the cells was 1×10⁵ cells/50 μL, the cells reached the evaluation value 3 in all of the wells after culture for 18 hours. In addition, as shown in Tables 16 and 17, in any of the conditions, the survival rates of the cells in the cell suspensions in which a promoter was present were equal to or higher than the survival rates of the cells in the cell suspensions in which a promoter was absent. In particular, in the cell suspension in which the number of the cells was 1×1.0³ cells/50 μL the cell suspension in which the number of the cells was 1×10⁵ cells/50 μL, and the cell suspension in which the number of the cells was 1×10⁶ cells/50 μL, the survival rates of the cells in the cell suspensions in which a promoter was present were critically higher than the survival rates of the cells in the cell suspensions in which a promoter was absent.

INDUSTRIAL APPLICABILITY

In the method of promoting spheroid formation according to the present invention, it is possible to form a spheroid in a fast and stable manner by convenient steps by using a promoter. For this reason, in clinical sites, for example, since it is possible to form a spheroid in a fast and stable manner using cells collected from patients, it is possible to significantly reduce stress or time in a drug sensitivity test of the cells derived from patients and the like. In addition, it is possible to perform analysis on cases in which spheroid formation has not been good so far and there is a difficulty in analysis.

While preferred embodiments of the invention have been described and shown above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A method of promoting spheroid formation comprising:
   preparing a mixture obtained by mixing a cell sample with heparin, wherein the cell sample comprises cells derived from an animal wherein the mixture comprises the heparin at a concentration of 1 to 10 mg/ml, wherein the cells are suspended in the mixture and in contact with molecules of the heparin;
   subjecting the mixture comprising the cells and the heparin at the concentration of 1 to 10 mg/ml to a centrifugal treatment in a spheroid formation-culture vessel to promote formation of a spheroid; and
   culturing, inside the spheroid formation-culture vessel, the cells with the heparin at the concentration of 1 to 10 mg/ml in the mixture, after subjecting the mixture to the centrifugal treatment, thereby forming the spheroid.

2. The method of promoting spheroid formation according to claim 1, wherein
   mixing the cell sample with heparin is repeatedly performed.

3. The method of promoting spheroid formation according to claim 1,
   wherein the number of cells included in the cell sample is 1×10³ to 1×10⁶ cells to form a single spheroid.

4. The method of promoting spheroid formation according to claim 1, wherein
   the cell sample contains the cells collected from a human.

5. The method of promoting spheroid formation according to claim 1, wherein
   the cell sample contains a plurality of kinds of cells.

* * * * *